(12) United States Patent
Marti et al.

(10) Patent No.: US 11,350,997 B2
(45) Date of Patent: Jun. 7, 2022

(54) HIGH-SPEED OPTICAL TRACKING WITH COMPRESSION AND/OR CMOS WINDOWING

(71) Applicant: Atracsys Sàrl, Puidoux (CH)

(72) Inventors: Gaëtan Marti, Le Mont-sur-Lausanne (CH); Maurice Hälg, Savigny (CH); Bernard Maxveil Arulraj, Fribourg (CH)

(73) Assignee: Atracsys Sàrl, Puidoux (CH)

( * ) Notice: Subject to any disclaimer, the term of this patent is extended or adjusted under 35 U.S.C. 154(b) by 89 days.

(21) Appl. No.: 16/855,114

(22) Filed: Apr. 22, 2020

(65) Prior Publication Data

US 2020/0345428 A1 Nov. 5, 2020

Related U.S. Application Data

(63) Continuation of application No. 16/485,903, filed as application No. PCT/IB2018/050899 on Feb. 14, 2018, now Pat. No. 11,013,562.

(Continued)

(51) Int. Cl.
*G06K 9/00* (2022.01)
*A61B 34/20* (2016.01)
(Continued)

(52) U.S. Cl.
CPC ............. *A61B 34/20* (2016.02); *A61B 90/39* (2016.02); *G06T 7/11* (2017.01); *G06T 7/246* (2017.01);
(Continued)

(58) Field of Classification Search
CPC ............ A61B 34/20; A61B 2034/2055; A61B 2090/365; A61B 2090/3983;
(Continued)

(56) References Cited

U.S. PATENT DOCUMENTS 5,603,318 A * 2/1997 Heilbrun ................. A61B 5/06
600/426
6,167,295 A * 12/2000 Cosman ................ A61B 90/10
600/414

(Continued)

FOREIGN PATENT DOCUMENTS

| WO | 2002076302 A2 | 10/2002 |
|----|---------------|---------|
| WO | 2016139638 A1 | 9/2016 |
| WO | 2017208186 A2 | 12/2017 |

OTHER PUBLICATIONS

International Search Report and Written Opinion for PCT/IB2018/050899 dated Jun. 13, 2018.

(Continued)

*Primary Examiner* — Shervin K Nakhjavan
(74) *Attorney, Agent, or Firm* — DLA Piper LLP

(57) ABSTRACT

A high-speed optical tracking with compression and CMOS windowing for tracking applications that require high-speed and/or low latency when delivering pose (orientation and position) data. The high-speed optical tracking with compression and CMOS windowing generally includes an optical tracking system (10) that sense fiducial (22) and by extension markers (20). The markers can either be integrated on tools (20) handled by an operator (e.g. surgeon) (50) or fixed on the subject to track (e.g. patient) (40). The low-level processing (101, 107, 140) is realized within the tracking system to reduce the overall data to be transferred and considerably reduce the processing efforts. Pose data (127) are finally computed and transferred to a PC/monitor (30,31) or to tablet (60) to be used by an end-user application (130).

36 Claims, 9 Drawing Sheets

Related U.S. Application Data

(60) Provisional application No. 62/458,697, filed on Feb. 14, 2017.

(51) Int. Cl.

| | |
|---|---|
| *A61B 90/00* | (2016.01) |
| *G06T 7/11* | (2017.01) |
| *G06T 7/246* | (2017.01) |
| *G06T 7/73* | (2017.01) |

(52) U.S. Cl.
CPC ........ *G06T 7/73* (2017.01); *A61B 2034/2055* (2016.02); *A61B 2034/2057* (2016.02); *A61B 2034/2065* (2016.02); *A61B 2090/3937* (2016.02); *A61B 2090/3945* (2016.02); *A61B 2090/3983* (2016.02); *G06T 2207/10052* (2013.01); *G06T 2207/30204* (2013.01)

(58) Field of Classification Search
CPC .... A61B 2034/2051; A61B 2090/3945; A61B 2034/2068; A61B 6/12; A61B 2090/363; A61B 8/4245; A61B 5/064; A61B 2034/2046; A61B 34/00; A61B 5/0033; A61B 8/403; A61B 8/5238; A61B 8/5246; A61B 8/565; G06T 7/246; G06T 7/74; G06T 7/70; G06T 9/00; G06F 3/011; G06F 3/0304; G06F 3/0346; G06K 9/3216; G06K 2009/3225; G06K 19/06009; G06K 2009/3291; G06K 2209/05; G06K 7/10861; G06K 9/3241; G06K 9/4661; G02B 2027/0138; G02B 2027/014

See application file for complete search history.

(56) References Cited

U.S. PATENT DOCUMENTS

| | | | | |
|---|---|---|---|---|
| 9,094,615 | B2* | 7/2015 | Aman | G06K 9/00711 |
| 9,214,023 | B2* | 12/2015 | Berlinger | G06T 7/74 |
| 10,348,404 | B1* | 7/2019 | Herman | H04B 10/116 |
| 2005/0162512 | A1* | 7/2005 | Seakins | G09B 21/00 |
| | | | | 348/62 |
| 2006/0283952 | A1* | 12/2006 | Wang | G06K 7/10 |
| | | | | 235/462.01 |
| 2007/0018389 | A1* | 1/2007 | Downs, III | A63F 1/14 |
| | | | | 273/149 R |
| 2007/0199998 | A1* | 8/2007 | Kotlarsky | G06K 7/10801 |
| | | | | 235/462.45 |
| 2008/0287781 | A1* | 11/2008 | Revie | A61B 90/36 |
| | | | | 600/426 |
| 2009/0161827 | A1* | 6/2009 | Gertner | A61N 5/1017 |
| | | | | 378/65 |
| 2010/0111489 | A1* | 5/2010 | Presler | H04N 13/239 |
| | | | | 386/278 |
| 2010/0176952 | A1* | 7/2010 | Bajcsy | A61B 5/6887 |
| | | | | 340/573.1 |
| 2011/0015521 | A1* | 1/2011 | Faul | A61N 5/1049 |
| | | | | 600/426 |
| 2011/0025853 | A1* | 2/2011 | Richardson | H04N 5/247 |
| | | | | 348/159 |
| 2011/0098553 | A1* | 4/2011 | Robbins | A61B 90/37 |
| | | | | 600/410 |
| 2012/0038748 | A1* | 2/2012 | Lindgren | B60R 1/00 |
| | | | | 348/47 |
| 2012/0262365 | A1* | 10/2012 | Mallinson | G06F 3/0325 |
| | | | | 345/156 |
| 2013/0225942 | A1* | 8/2013 | Housing | G06T 7/12 |
| | | | | 600/301 |
| 2015/0335390 | A1* | 11/2015 | Gill | A61B 34/20 |
| | | | | 600/424 |
| 2016/0000518 | A1* | 1/2016 | Thoranaghatte | G06F 3/017 |
| | | | | 703/11 |
| 2016/0199148 | A1* | 7/2016 | Maracaja-Neto | A61B 90/39 |
| | | | | 600/424 |
| 2016/0379684 | A1* | 12/2016 | Anderson | G06K 9/00751 |
| | | | | 386/227 |
| 2017/0086941 | A1 | 3/2017 | Marti et al. | |
| 2017/0231702 | A1* | 8/2017 | Crawford | A61B 10/0275 |
| | | | | 700/254 |
| 2018/0071032 | A1* | 3/2018 | de Almeida Barreto | |
| | | | | A61B 34/10 |
| 2020/0129240 | A1* | 4/2020 | Singh | A61B 5/00 |

OTHER PUBLICATIONS

Muehlmann et al."A New High Speed CMOS Camera for Real-Time Tracking Applications" Apr. 26, 2004, Robotics and Automation 5:5195-5200.

Ribo et al. "A New Optical Traacking System for Virtual and Augmented Reality Applications" May 21, 2001, Proceedings of the 18th IEEE Instrumentation and Measurement Technology Conference 3:1932-1936.

* cited by examiner

Conventionnal sensor :

CMOS sensor with windowing :

The following graph shows the histogram of the readout ratio:

HIGH-SPEED OPTICAL TRACKING WITH COMPRESSION AND/OR CMOS WINDOWING

CORRESPONDING APPLICATION

The present application is a continuation of U.S. application Ser. No. 16/485,903, filed Aug. 14, 2019, which is a U.S. national stage filing under 35 U.S.C. § 371 of International PCT Application No. PCT/IB2018/050899, filed Feb. 14, 2018, which claims priority to the earlier US provisional application USSN 62/458,697, filed on Feb. 14, 2017, the content of each earlier application being incorporated by reference in its entirety in the present application.

TECHNICAL FIELD AND BACKGROUND OF THE INVENTION

The present invention relates generally to hi-speed optical tracking and more specifically it relates to a high-speed optical tracking with compression and CMOS windowing for tracking applications that require high-speed and/or low latency when delivering pose (orientation and position) data.

Typically, such optical tracking systems are used in the field of computer assisted surgery or dentistry, robotic assisted surgery or dentistry, rehabilitation and other similar medical applications. On a more general level, they are used in the fields of industrial part checking, or other applications where the tracking is required.

Traditional optical pose tracking systems comprise two or more cameras. They use triangulation to determine the 3D position of light generating elements in space. These light generating elements may either be active: they transmit light (e.g. LEDs) or passive: they reflect light (e.g. reflective disks or spheres), or a combination of active and passive. In the passive case, the light used to be generated on rings of LEDs located around the cameras of the optical tracking system. Emitted light is further reflected on tracked objects and sensed by the cameras.

Such tracking systems are able to compute (that is determine) the 3D position of every single light generating element. If at least 3 light generating elements with known relative positions are measured, it is further possible to compute (that is determine) a 3D orientation. Such an object is called a marker and markers are fixed on target objects/subjects to be tracked by the system.

In a medical application context, a user (e.g. a surgeon) touches a region of interest on the patient's body using a distal tip of an object (e.g. a probe or a surgical instrument). A tracking system views the marker(s) affixed to the object and is able to retrieve its/their pose(s). Then, on the basis of the known relationship between the location of the marker(s) and the location of the object tip, the marker-tracking system determines the coordinates of the object's tip as well as it's orientation. Such pieces of information can be used for example by an application to register the patient with a preoperative planning and/or to steer the interventional radiologist when inserting a biopsy needle.

Moreover, medical and especially surgical applications require the markers to be sterile. Common passive markers are usually disposable, autoclavable or a mix of the two.

Examples of tracking systems and methods are given in publications WO 2017/208186 and US 2017/0086941.

BRIEF SUMMARY OF THE INVENTION

The invention generally relates to a hi-speed optical tracking which includes an optical tracking system (10) that sense fiducials (22) (by extension markers 20). The fiducials (respectively markers) can either be integrated on tools (20) handled by an operator (e.g. surgeon) (50) or fixed on the object/subject to track (e.g. patient) (40). The low-level processing (101, 107, 140) is preferably realized within the tracking system. Pose data (127) are computed and transferred to a PC/monitor (30, 31) or to a tablet (60) to be used by an end-user application (130).

There has thus been outlined, rather broadly, some of the features of the invention in order that the detailed description thereof may be better understood, and in order that the present contribution to the art may be better appreciated. There are many additional features of the invention that will be described hereinafter.

In this respect, before explaining at least one embodiment of the invention in detail, it is to be understood that the invention is not limited in its application to the details of construction or to the arrangements of the components set forth in the following description or illustrated in the drawings. The invention is capable of other embodiments and of being practiced and earned out in various ways according to different embodiments. Also, it is to be understood that the phraseology and terminology employed herein are for the purpose of the description and should not be regarded as limiting.

In a first aspect, an object and aim of the present invention is to improve the known devices and methods.

Another object is to provide a high-speed Optical Tracking with compression and/or CMOS windowing for tracking applications that require high-speed and/or low latency when delivering pose (orientation and position) data.

Another object is to provide a High-speed Optical Tracking with Compression and/or CMOS Windowing that improves the tracking speed and reduce the latency of pose data delivery.

Another object is to provide a High-speed Optical Tracking with Compression and/or CMOS Windowing that enables high-speed/low latency within embedded processing as less data are to be processed with respect to a conventional solution (that would not have these features).

Another object is to provide a High-speed Optical Tracking with Compression and/or CMOS Windowing that enables to transfer and process raw data within a compressed form.

Another object is to provide a High-speed Optical Tracking with Compression and/or CMOS Windowing that uses CMOS windowing and image-based object tracking to speed-up the readout phase of the imaging sensor.

Another object is to provide a High-speed Optical Tracking with Compression and/or CMOS Windowing that uses an additional micro-lens array in the front of the image sensor to enable light field applications (e.g. simultaneously acquiring 2D images and 3D depth maps).

Another object is to provide a High-speed Signal Processing with Compression and/or CMOS Windowing to speed-up the data acquisition with respect to a conventional solution.

Other objects and advantages of the present invention will become obvious to the reader and it is intended that these objects and advantages are within the scope of the present invention. To the accomplishment of the above and related objects, this invention may be embodied in the form illustrated in the accompanying drawings, attention being called to the fact, however, that the drawings are illustrative only, and that changes may be made in the specific construction illustrated and described within the scope of this application which is not limited to the exemplary embodiments described herein.

In an embodiment, the invention concerns a method for high speed tracking of optical fiducials and markers, wherein
- at least one fiducial is attached on a marker which is placed on an object and/or on a person, said fiducial is detected by at least one optical sensor, said optical sensor providing sensor data;
- the position and/or orientation of said marker(s) detected by said optical sensor is determined by a data processing step of said sensor data;
- the determined position and/or orientation is transmitted through communication means as processed data to an application for further treatment, wherein in the data processing step said sensor data is transferred to a compression module for compression of said sensor data and wherein said position and/or orientation of said marker is determined from said compressed data.

In an embodiment, the sensor data readout is partial, meaning that only a part of the sensor data is read and used for subsequent treatment, whereby said readout contains sufficient information for the determination of the fiducials to be tracked.

In an embodiment, the partial sensor data of said fiducials is not compressed for the determination of said position and/or orientation of said marker.

In embodiments of the invention, the data may be compressed or not and/or partial or not. Preferably, the acquired data is treated (for example compressed and/or partial, i.e. windowed) to reduce the overall size of data and reduce treatment time.

In an embodiment, in the data processing step of the method, the compressed or not-compressed data is segmented depending on the intensity of the pixels.

In an embodiment, after segmentation of the data, blobs are detected in the segmented image and their position determined.

In an embodiment, a geometry matching is made between a cloud of 3D reconstructed points and the geometry of the object.

In an embodiment, the further treatment of data comprises a navigation application for tracking said optical fiducials and/or markers.

In an embodiment, the data are used to control a robotic structure.

In an embodiment, the robotic structure is used in a surgical application.

In an embodiment, the robotic structure is held by an operator, such as a surgeon. For example, the robotic structure may be an intelligent tool such as the NAVIO™ surgical system manufactured by the Company Smith Nephew and disclosed for example at the following link http://www.smith-nephew.com/professional/microsites/navio/.

Other robot and device may of course use the present invention as well, this example being non-limiting.

The present invention also concerns a device for the high speed tracking of optical fiducials and markers according to one of the preceding clauses, comprising
- at least a fiducial attached to a marker placed on an object and/or a person,
- an optical tracking system with an optical sensor detecting said fiducial(s) or said marker(s) via sensor data,
- electronic means, comprising at least a memory and sensor data treatment means for determining the position and/or orientation of said marker(s) detected by said sensor by treatment of sensor data,
- communication means to transfer the determined position and/or orientation of said marker(s) to an application for further treatment, wherein the data treatment means comprise at least a compression module for compression of said sensor data and wherein said position and/or orientation of said marker is determined from said compressed data by said treatment means.

In an embodiment, said treatment means receive partial sensor data from a window of said sensor.

In an embodiment, the device comprises an electronic device receiving said determined position and/or orientation, said electronic device being a computer device.

In an embodiment, the computer device is a tablet or another equivalent device.

In an embodiment, the object is marker.

In an embodiment, the transfer of data is made via wireless means. Of course, the transmission may also be made via wire or a combination of wire and wireless.

In an embodiment, the optical sensor comprises a least one camera.

In an embodiment, the device is used to control a robotic structure.

In an embodiment, the robotic structure is used in a surgical application.

In an embodiment, the robotic structure is an intelligent tool and may be held by an operator, such as a surgeon. The robotic structure may be the Navio™ surgical system disclosed above or another equivalent structure/device.

In an embodiment, at least one optical sensor used m the method and the device may be a plenoptic camera.

In an embodiment, the plenoptic camera may comprise a micro-lens array placed m front of the sensor array, each micro-lens and the underlying pixels on the sensor array forming a micro-camera.

In an embodiment, the partial sensor data read in the method may be defined to retrieve only specific micro-camera pixels.

In an embodiment, the information from at least one micro-camera may be used to define a rough position of the fiducials in the images.

All technical means of the embodiments of the invention will be described in more detail in the following description of the invention and its features.

BRIEF DESCRIPTION OF THE DRAWINGS

Various other means, objects, features and attendant advantages of the present invention will become fully appreciated as the same becomes better understood when considered in conjunction with the accompanying drawings, in which like reference characters designate the same or similar parts throughout the several views, and wherein:

FIG. 1 is an upper perspective view of a computer assisted surgery (CAS) setup for a typical registration step using optical tracking. The optical tracking system (10) is composed of two cameras (11), surrounded by infrared lights rings (11). The device is connected to a computer trough a cable (32) (e.g. USB, Ethernet, etc.). The optical tracking system (10) detects fiducials (22) (e.g. reflective material or infrared emitting diodes) that are in the field of view of the cameras. Fiducials that are rigidly affixed at a known position define a marker (21). A pointer (20) is a marker with a tool-tip that is used to point anatomical landmarks. The marker (21) is rigidly fixed (e.g. screwed, taped, etc.) on the patient (40). The pointer is hold by the surgeon (50) which records anatomical landmarks on the patient (40). Corresponding landmarks are at the same time visible on the screen (31). The screen is connected to the PC via a cable (33). The correspondence between virtual and pointed landmarks is called registration and allows to know the position of the marker in the virtual reference. Registration is used in a CAS application to put in correspondence the planning and the real patient.

FIG. 2 is an upper perspective view of a compact computer assisted surgery setup for a typical registration step using optical tracking. The process is similar to FIG. 1 except that it is more embedded and compact. In this example, the optical tracking system (10) has embedded computing capacities (13). Instead on being connected to an external computer, the connection between the cameras (11) and the embedded computing unit is done internally (34), for example within the system (10). Note that the cable on the image is only for illustration. This link would practically and preferably be integrated in an electronic circuitry. After internal pose computation, data are transferred wirelessly (61) (e.g. through a WiFi, Bluetooth™ or LiFi connection) to a tablet PC (60). The end user application (APP) runs on the tablet.

FIG. 3 is a flowchart of a conventional optical tracking system. Fiducials (22) are sensed by camera sensors (e.g. CMOS—11). For each camera, pixels of the entire image or a sub-part of it are readout (105) to a memory (110). Images are then retrieved by the data processing unit (120) either via a wired link to an external PC (see FIG. 1), or through an internal bus in case of an embedded processor (see FIG. 2). The data processing unit first segments the image depending on the intensity of the pixels (121), detects blobs (122) in the segmented images, find their centroids, the right and left correspondence (123), and further determines their 3D position by mean of triangulation (124). The correspondence between the cloud of 3D points and the geometry of the markers is optionally performed. This step is called geometry matching (125). If a marker (21) comprises three or more fiducials (22), it is possible to compute its pose (position and orientation—126). Pose data (127) are finally transferred to the navigation application (130) (e.g. The registration Software application described in FIG. 1).

FIG. 4 is a flowchart illustrating the overall operation of an embodiment of the present invention. Fiducials (22) are sensed (i.e. detected) by camera sensors (11). Camera sensors are connected to a low-level tracking engine (101) that determine a window or several windows in the image provided by the sensor (11) where are located the fiducials (22), respectively the markers to track (20, 21). Partial images are readout from the sensors (106) and further transferred to an image compression module (107) that will reduce the memory footprint (size) of the sub-images defined by the windows. This compression will also enable to later process the images without requiring to decompress them (140). Compressed images are further stored in the memory (110). The compressed data processing unit (140) retrieves the partial compressed images. It first segments the image depending on the intensity of the pixels (141) directly using the compressed images (without requiring any preliminary decompression), detects blobs (142) out of segmented image, defines their centroids, finds the right and left correspondence (143), and determines their 3D position by mean of triangulation (144). The correspondence between the cloud of 3D points and the geometry of the markers is optionally performed. This step is called geometry matching (145). Pose data (127) are finally transferred to the naviga- tion application (130). As mentioned above, in one embodiment, partial images are readout and the corresponding data is compressed. In another embodiment, one may envisage to compress the data of the entire image (and not only of partial images) or alternatively to use directly the data of partial images without compression of data. Depending on the performance and capabilities of the system, this may be enough to ensure the desired tracking speed. However, if possible, the compression of partial data is a preferred method.

FIG. 5 presents the timing diagram of a conventional sensor (up) versus a sensor using windowing (down). Note that for a sensor using windowing, the sensor integration time is the same but the readout is considerably reduced. In both situations, the readout time is directly proportional to the number of effective pixels to retrieve.

FIG. 6 is an upper perspective view of a robotic assisted surgery setup using optical tracking. The process is similar to FIG. 2 except that the human operator (50) is replaced by a robotic arm (51). The end-effector of the robot (52) holds a marker (20) and a surgical tool (53). The geometric relation between the marker and the surgical tool is known. Note that the transformation between the patient (via the marker) and the surgical tool is used to steer the robot during the operation process. It enables to control the robot's movements even if the patient's anatomy is moving. Low latency and fast update rates of the optical pose estimation are required to safely and precisely control the robot. It also has an impact on the operating speed that could be increased.

FIG. 7 is an upper perspective view of an intelligent tool (54) in a computer assisted surgery setup using optical tracking. An intelligent tool is defined as being a handheld robot. The intelligent tool is held by the surgeon and moves given the relation between the marker and the patient position. As such, it is similar to setup of FIG. 6, except that the base of the robot is not fixed and is held by the operator.

DETAILED DESCRIPTION OF THE INVENTION

A. Overview

Figure 1:
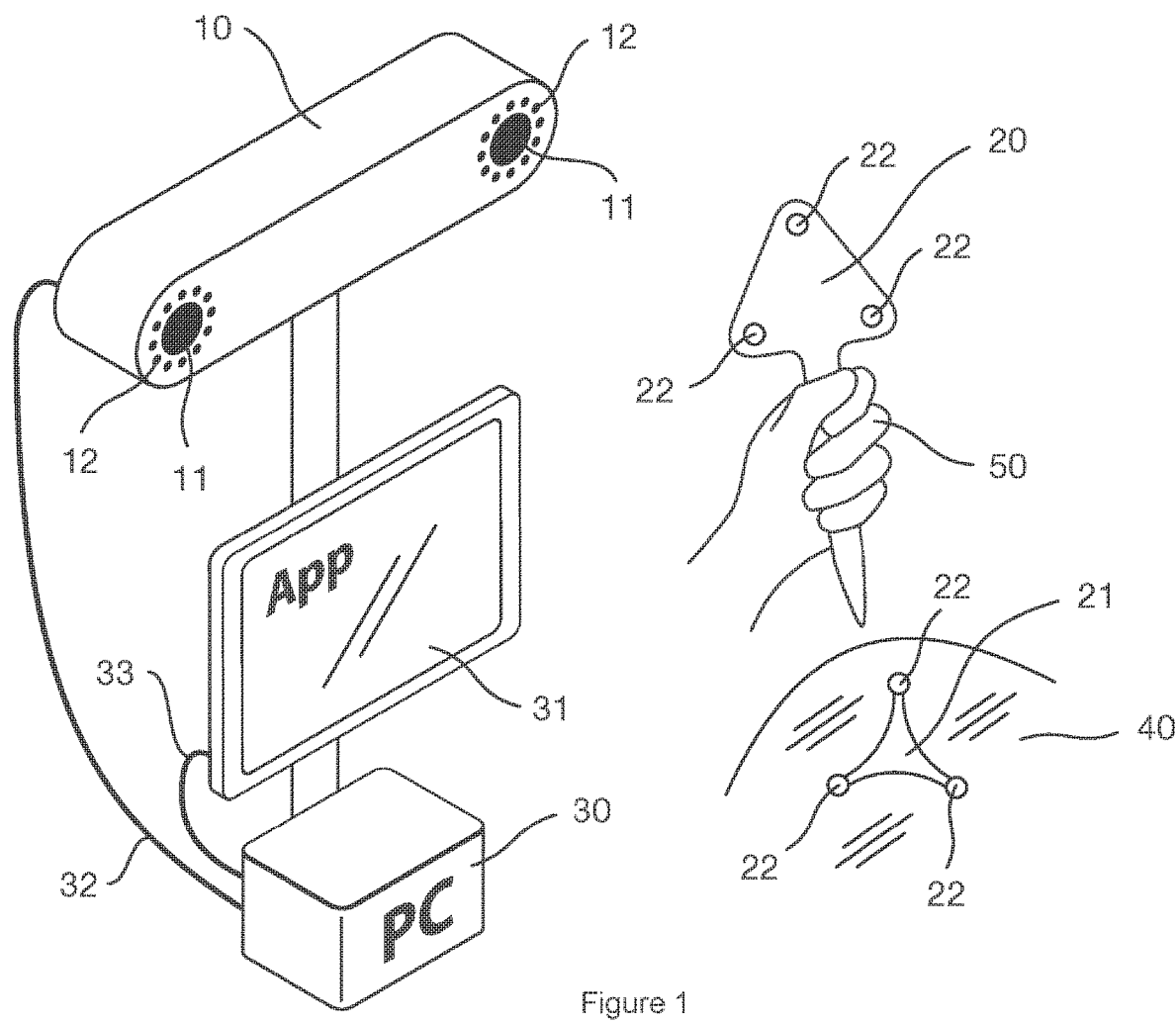
FIG. 1.

Turning now descriptively to the drawings, in which similar reference characters denote similar elements throughout the several views, the figures illustrate an optical tracking system (10) that sense fiducials (22). A marker (20) is formed by three or more fiducials fixed together at known locations. The markers can either be integrated within/on tools (20) held by an operator (e.g. a surgeon, or a robot) (50) or fixed on the object/subject to track (e.g. a patient) (40). The low-level processing (101, 107, 140) is preferably realized within the tracking system. Pose data (127) are computed internally and sent to a tablet (60) or transferred and computed on an external PC (30). Poses are finally used by an end-user application (130). The overall system is designed to improve the overall performances (e.g. improve speed, reduce latency) by reducing the quantity of data to transfer during the processing and thereby win time, for example.

B. Optical Tracking System

The optical tracking system comprises one or more cameras (11). The device emits infrared light from rings (12), for example using IR LEDs surrounding each infrared camera. Cameras are sensing fiducials (22) placed on objects/subject to track like markers (20, 21).

There are mainly two types of fiducials, both being possible in embodiments of the present invention, either as alternative solutions, or in combination:

1. Passive fiducials which are coated with a retro-reflective material containing small spheres that mirror the light (for example from the IR LEDs of the ring 12) back to the lenses, causing the fiducials to appear as bright spots in the infrared images.
2. Active fiducials which are light sources (e.g. infrared light emitting diodes—IR—LEDSs). When using exclusively such fiducials, the rings (12) are then not necessary.

Raw data are further processed (101, 107, 140) to provide 3D position of the fiducials. When three or more detected fiducials are part of markers, it is possible to compute their poses.

Most commonly used tracking systems are stereo-cameras (system comprising two cameras) which are fixed on a baseline. The transformation from one camera to the other is usually factory calibrated or alternatively calibrated in the field. Once a fiducial is simultaneously detected by both cameras, it is possible to compute its 3D position by means of triangulation. Example of commonly used passive optical tracking systems are for example Atracsys infiniTrack™, fusionTrack™, spryTrack™, Northern Digital Polaris™, and Axios CamBar™.

Optical tracking systems usually operate in the near infrared spectrum but can alternatively be designed for the visible spectrum or any other spectrum.

Optical tracking systems can alternatively detect tags or known pattern. Systems like ARToolkit™ (http://artoolkit.org) or MicronTracker™ from the company ClaroNav are tracking objects with specific tags. Tags/patterns are not to be considered as fiducials.

Tags/patterns have feature points (see features points on Wikipedia). These feature points then form fiducials, whereas tags/patterns are to be considered as markers m the context of the present invention. Other equivalent marking means (fiducials or markers) are of course possible m the scope of the present invention.

Optical tracking systems with three or more cameras are alternatively possible in other embodiments of the invention.

Other types of setup are also possible like fixing single tracking cameras in the room and having an extra calibration step to define their respective transformation. This methodology is usually used for motion capture applications. It is alternatively possible to fix several multiple camera tracking systems (with a known baseline) in the room.

Figure 2:
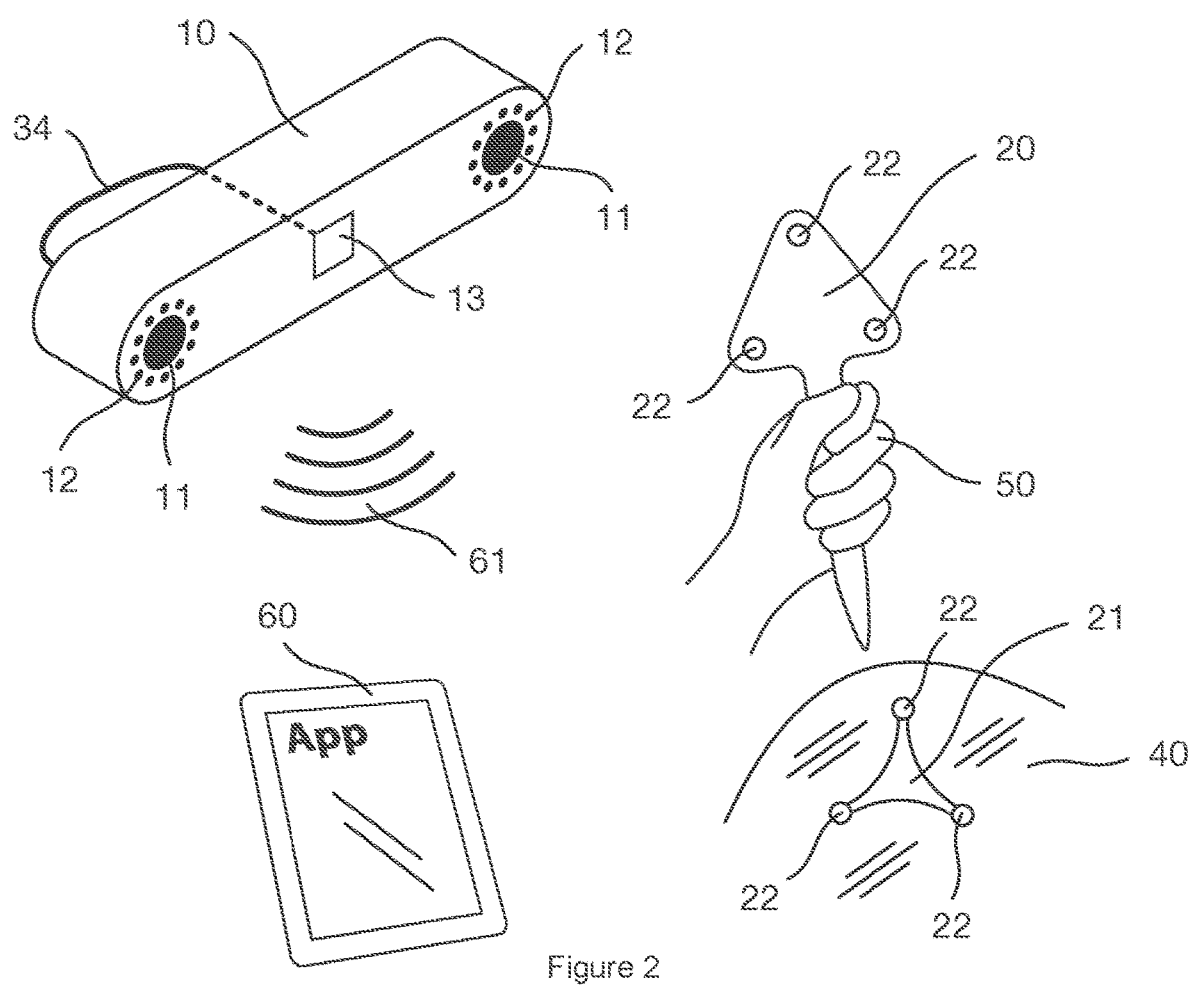
FIG. 2.
Figure 3:
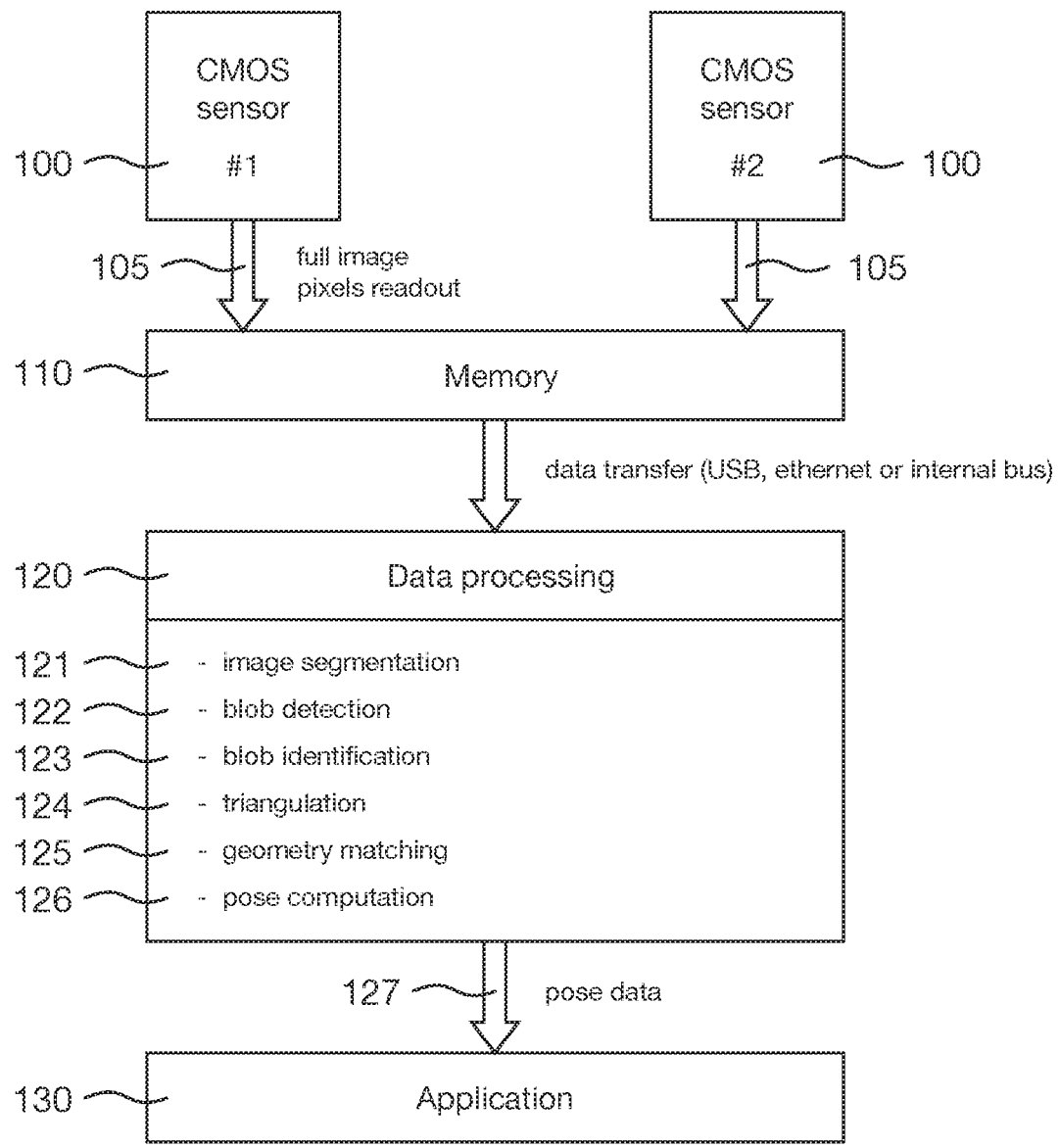
FIG. 3.
Figure 4:
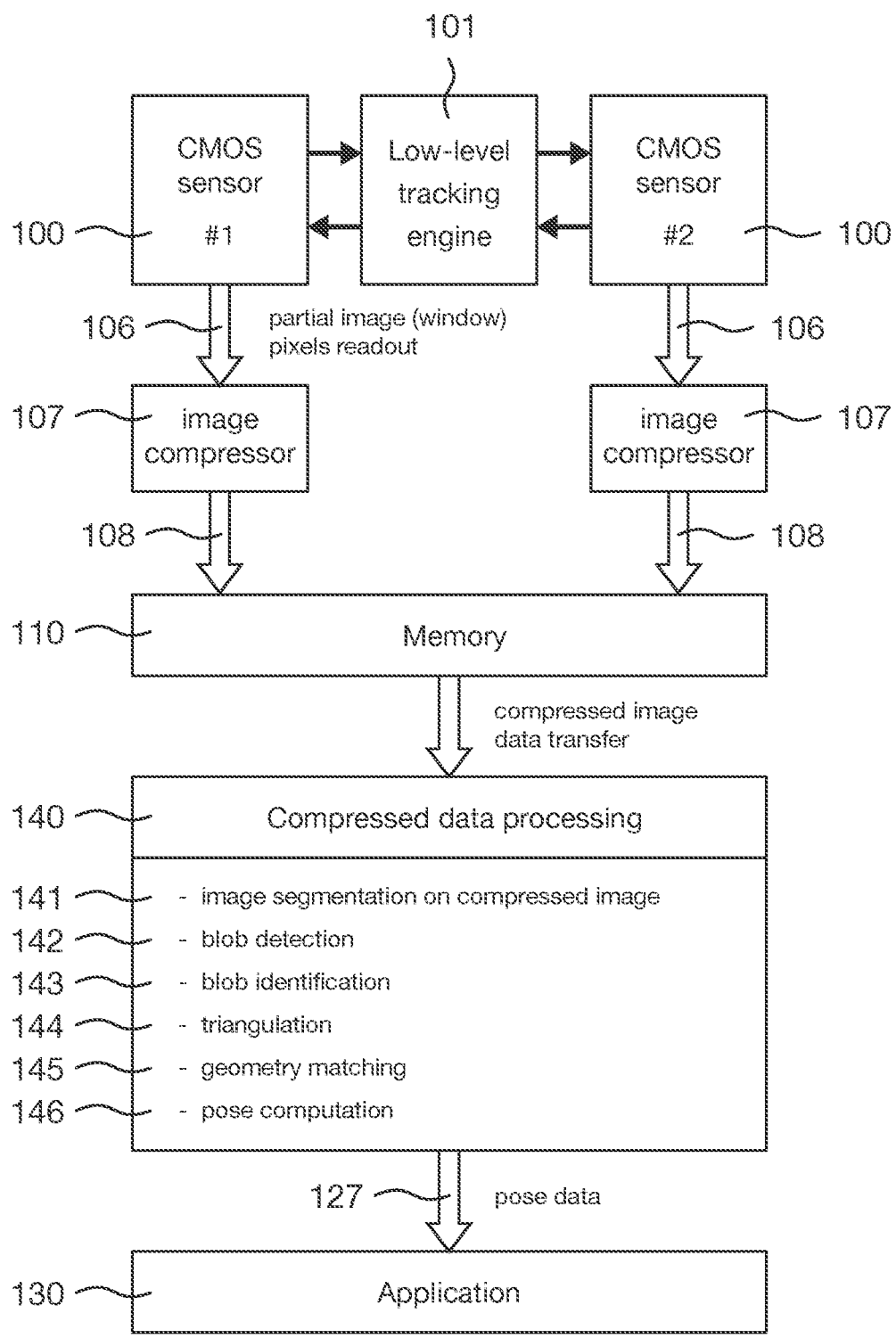
FIG. 4.
Figure 5:
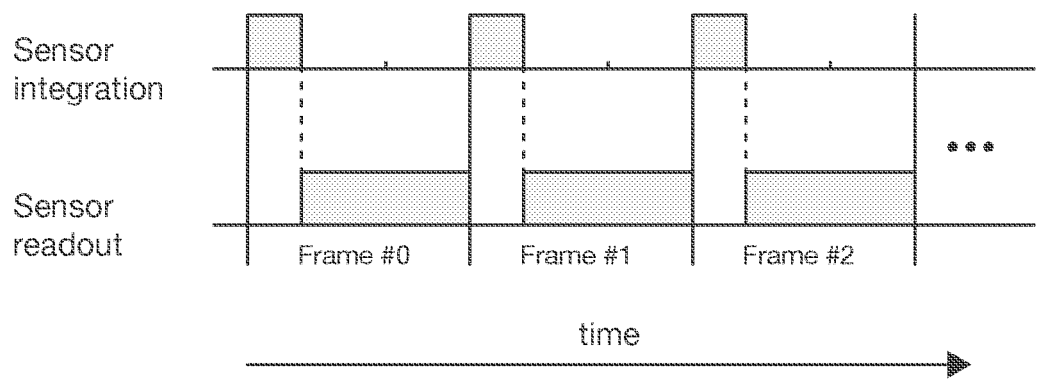
FIG. 5.
Figure 5:
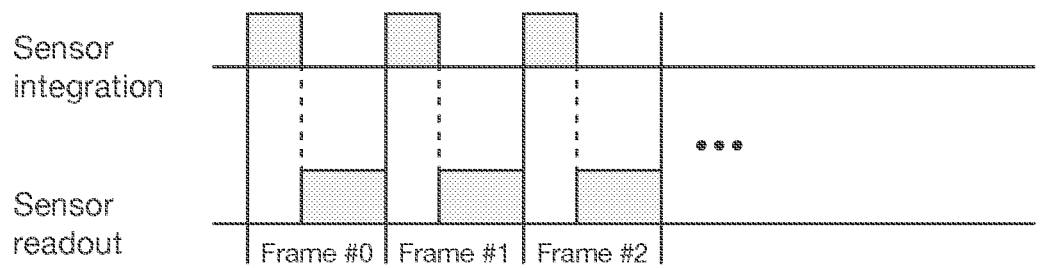

Systems capturing active fiducials (e.g. Infrared LEDs) do not need to have the ring of LEDs (12) described on FIG. 1 and FIG. 2 but they may be present (but not used) in order to provide standard products Optical tracking systems may have embedded processing capabilities (e.g. FIG. 2) or delegated processing (e.g. FIG. 1). By delegated processing, the pose computation from the raw signals is partly realized within the tracking system and partly on an external CPU like a PC. One configuration or the other may be chosen according to circumstances.

C. Tracked Tools

A tracked tool comprises a marker rigidly fixed to (respectively integrated in) an instrument (20). The marker—also called rigid body in the literature—(20, 21) comprises several fiducials (22) rigidly fixed altogether. The relative position of the fiducials forming the marker is called the geometry and should be well known in order to estimate the pose of the marker from the 3D points of cloud. During the tracking process (140), these fiducials are detected (142), identified (143) and their 3D position is calculated by the tracking system by means of triangulation (144). If at least three fiducials are detected, the Arun registration algorithm ("Least-squares fitting of two 3-D point sets", Arun, 1987) can be used to calculate the pose (position+translation) of the marker in the tracking system referential. Note that a tracked tool may compose less than three fiducials. In this case, only reduced spatial information (less than 6 degrees of freedom) can be retrieved by the tracking system. Tracked tools are designed to be autoclaved or partly/entirely disposable in surgical applications.

The tracked tools may be a digitizer for registration purposes, or any surgical tools including drill, biopsy needle, or intra-operative imaging like ultrasound probe, endoscope, CT-scanner, Mill, robots, intelligent tools, etc.

Figure 6:
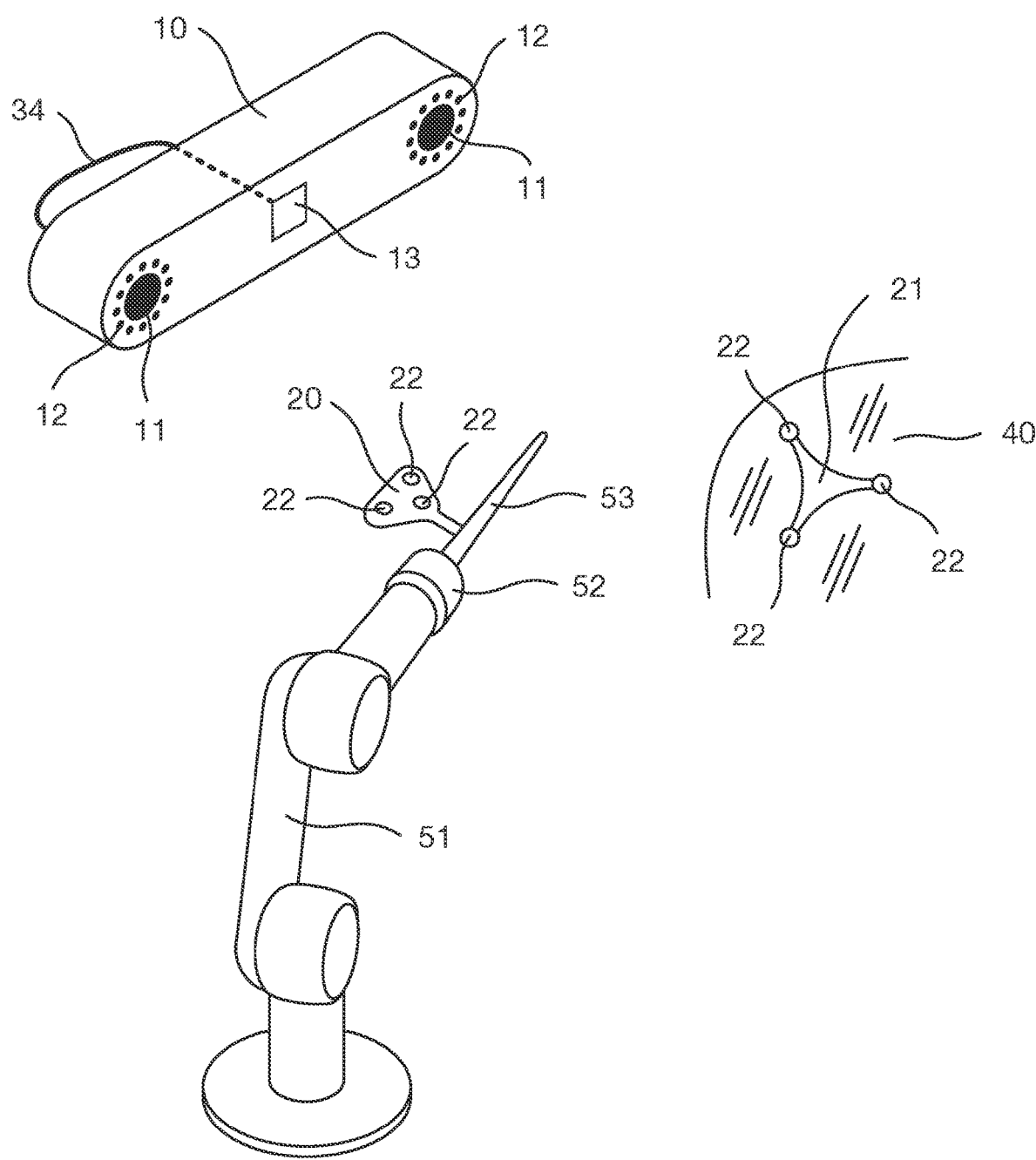
FIG. 6.
Figure 7:
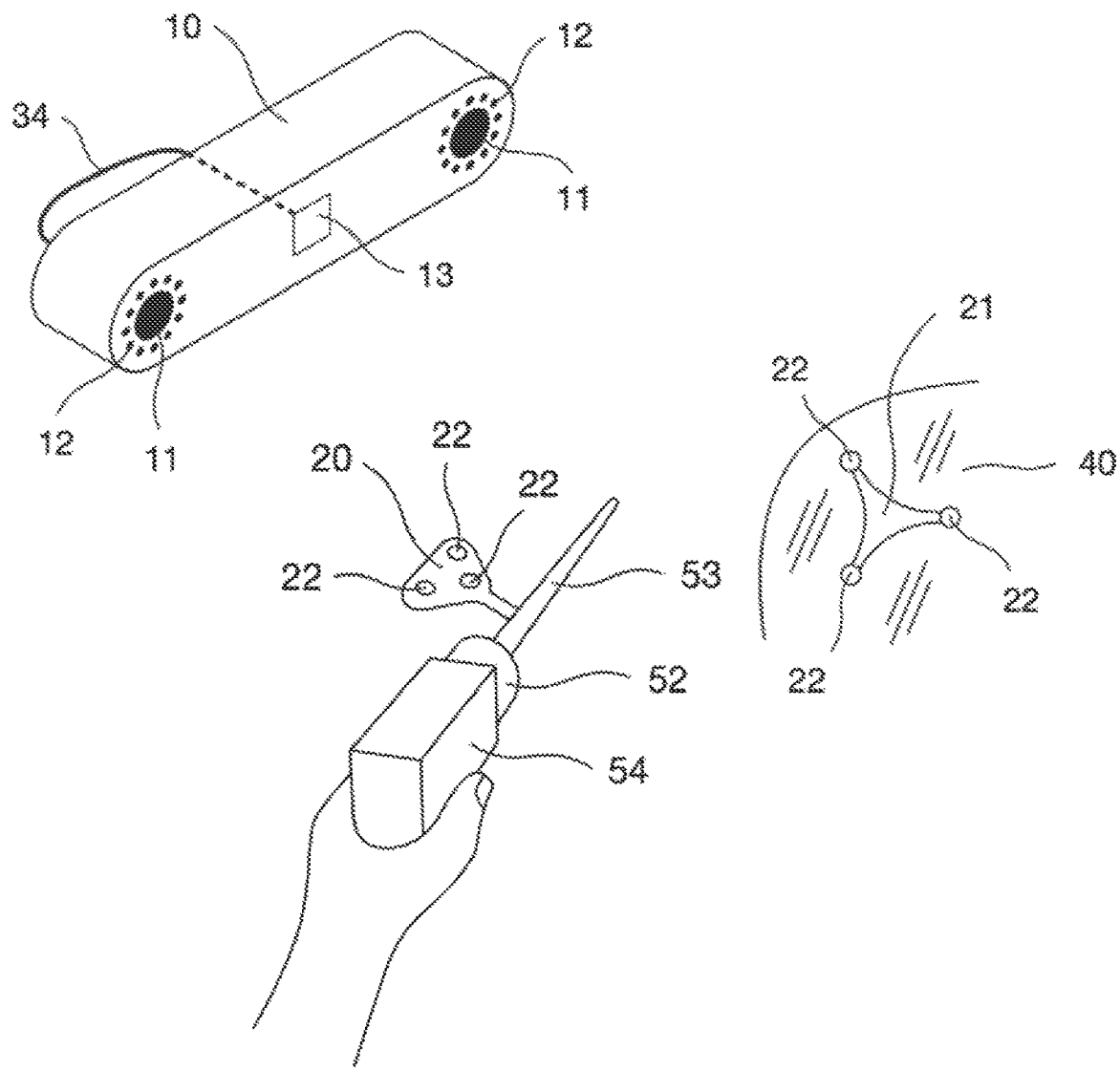
FIG. 7.

The tracked tool may be operated by a human operator (e.g. the surgeon) or a robot (see: FIG. 6) an intelligent tool (see FIG. 7), in an automatic, semi-automatic or manual manner. An example of robot is the Mako System™ from the company Stryker. An example of an intelligent tool is the NAVIO™ from Smith and Nephew.

D. PC System

The PC system alternatively called navigation PC (30) retrieves processed data (32), computes pose of the markers (20, 21) if this process has not already been done within the tracking system (13). The PC is connected (33) to a (touch-)screen (31) to display the end-user application (130).

Typical PC systems (including the screen) used m the Operating Room (OR) are placed on a cart and are fixed on a pole with a gimbal to aim the tracking zone.

The PC can run any operating system (windows, Linux, etc.).

The input device for the PC is any appropriate system such as a touch-screen, a mouse, a keyboard, a Kinect, etc.

E. Tracked Subject

The tracked subject (40) is typically a patient under surgery. The marker (21) is fixed (as rigidly as possible) on the anatomy targeted by the surgery. For example, during a hip replacement procedure, the marker can be fixed on a Steinmann's nail.

Different surgical procedures use navigation like implant placement, image-guided surgery, neuro, ENT, spine, maxillofacial, liver surgeries, dentistry and may benefit from the present invention. Markers (21) are fixed (screwed, taped, etc.) on the anatomy to track.

After registration step is realized, the marker should stay affixed to the anatomy, otherwise a re-registration is necessary.

F. Operator

The operator (50) holds the tracked instruments. In the application of FIG. 1, the surgeon uses a digitizer (20) to point anatomical landmarks on the patient (40). In a surgical application, the operator is the surgeon, assistant and/or nurse. The operator may alternatively be a robot or a combination of both in case of an intelligent tool G. Tablet The tablet (60) is similar to a PC having a touch-screen except that data transfer (61) is usually performed wirelessly.

Tablet may be a portable PC (e.g. Lenovo Yoga®), a phablet (Android®, iOS®, Windows®) a tablet (iPad®) or any mobile computer including a touch screen.

The tablet is usually medical grade and/or wrapped in a sterile bag to avoid contamination within the sterile field of the OR.

H. Camera Sensor

A camera sensor (11) comprises an image sensor and electronics to control it. For example, CMOS (Complementary Metal Oxide Semiconductor) image sensors (100) convert light into electric charge and process it into electronic signals. With this technology, each pixel has its own charge-to-voltage conversion, and the sensor often also includes amplifiers, noise correction, and digitization circuits, so that chip outputs are digital bits. A CMOS imager converts charge to voltage at the pixel, and most functions are integrated into the chip. CMOS technology has the ability to read out only a portion of the image (also called windowing mechanism) (106). This technique is used to increase the overall frame rates and reduce the latency as only small regions of interest (pixels) are readout and may typically be used in the present invention.

Sensors are linked to dedicated digital electronics to both control the chip (e.g. set the integration time, set the pixel depth retrieval, etc.), as well as estimate the position of the fiducials (22) within the images (101) to set the corresponding region of interest (windows) within the CMOS sensor. A smart windowing heuristic is able to reduce the readout time of the CMOS sensor—as less pixels are readout—by a factor typically ranging from 1.5 to 3 enabling to considerably speed up the entire acquisition process. An example of heuristic is presented later in the present description and may be applied in embodiments of the present invention.

Any image-sensor technologies having windowing capabilities may alternatively be used in embodiments of the present invention.

Partial images readout from the image sensor are further compressed (107). The image-compression algorithm is designed such that the image segmentation process (141) can be done without requiring (any/a full) decompression of the images. Resulting compressed images are further transferred (108) to a shared memory (110).

The camera sensor may comprise a CMOS image sensor, connected to a micro-controller or FPGA control circuit. The electronic to control the CMOS may alternatively be embedded on the chip (ASIC). The camera sensor may be fully designed for this task meaning that it will include the effective array of pixels, the windowing capabilities and the low-level tracking engine (101).

The camera lens may comprise a classic main lens or be composed with an additional micro-lens array allowing the image sensor to record 2D image and 3D depth information of a scene with a single capture (eg. https:/raytrix.de.technology, https://www.lvtro.com). The placement of an additional micro-lens array in front of the image sensor modifies the captured light on the sensor. Each single micro-lens creates a single image on the sensor, the size of that image being equal of the size of the pixels behind each single micro-lens (also known as a micro-camera). That captured sub-image represents the scene with a specific angle of view. The footprint of that image on the sensor is limited to the size of the micro-lens. It means that in that case, with a partial read-out capturing pixels from a unique micro-lens, the complete 2D overview view of the scene is accessible. That type of lens can be mounted on a tracking system, on one or multiple cameras to help the low-level tracking engine to fine-tune the windowing algorithm. The windowing algorithm could use that partial read-out to visualize the complete field of view even with a lower resolution. Noisy field of view can be easily identified with a predefined limited read-out time.

Such a light-field (aka plenoptic) camera allows among other things the refocusing of the depth of field on post-capture. The windowing algorithm can reconfigure on the fly the focus of the scene for each captured partial data from a unique single capture. Different criteria such as optical jitter of a blob or its size, its relative distance or the angle of view of the seen 3D marker can be considered.

That lens may be mounted on IR limited or visible spectrum ranged image sensor. Only 2D image partial or complete data can be processed without analysis of 3D depth information. 3D depth information can be partially reconstructed, even with a limited resolution.

That light-field camera may alternatively be used as an additional data source (2D and/or 3D image) synchronized or not with other cameras.

Any other light-field technology (e.g. multi-camera arrays) may alternatively be used.

I. Memory

The memory (110) stores the compressed partial images coming from the camera sensors modules (100). If the processing is embedded, the main processor will access (via an internal bus) these partial images for further processing. If the processing is done on an external PC, partial image data are transferred to the PC by a communication channel (32). This communication channel may be wired (e.g. USB, Ethernet, etc.) or wireless (e.g. Li-Fi, Wi-Fi, Bluetooth, etc.).

A fast memory is required to store the real-time flow of data. A RAM (e.g. DDR2, DDR3) is typically used for example.

J. End-User Application

Typical end-user application is dedicated for image-guided surgery, computer-assisted surgery, or robotic-assisted surgery.

Alternate applications for motion capture or rehabilitation may benefit from the proposed invention.

Alternate industrial application in the fields of quality control and reverse engineering may also be envisaged.

Other general purpose meteorological application may benefit from the invention.

K. Compressed Partial Images Processing

The goal of the compressed partial images processing (140) is to compute the pose estimation of the marker (146) from the raw compressed partial images with the minimum CPU resources and as fast as possible. The overall process is well known in the literature and can for example be found in the paper: "Affordable Infrared-Optical Pose-Tracking for Virtual and Augmented Reality", Tomas Pintaric, 2007, which is incorporated by reference m the present application. The originality of the proposed approach is to perform the processing without requiring to preliminary decompress the images data. It has the advantages to require less bandwidth to transfer and to process the data which will increase the update speed and reduce the overall latency.

The processing can basically be defined as followed: the compressed partial images are first segmented (141) to find the blobs. A blob is normally the image of a fiducial (but can alternatively be some noise). An example of such a compression algorithm is described later in the present description. The centroid of each candidate blob (142) is then computed using standard image processing techniques. The blobs are further identified (143) in order to determine which fiducial/marker they are from. As the geometry of the camera sensors (intrinsic and extrinsic parameters) (100) is known, it is possible to find the 3D positions of each fiducials by mean of triangulation (144). The system further tries to find the geometries of the markers within these reconstructed 3D points (145). Finally, the pose (orientation and position) of the markers and/or the 3D position of the individual fiducials is computed (146) and further transferred (127) to the end-user application (130).

This processing is done in an embedded processor like an FPGA (Field Programmable Gate Array), a SoC (System on Chip), a micro-controller, a CPU, a DSP or directly within a dedicated ASIC chip.

Captured partial image data moved into memory can leverage multiple optimization offered by the platform. A typical optimization could be to trigger an interrupt signal on each partial sets of data moved into memory. A set of data could be an aggregate of pixels to reconstruct one single blob.

The processing unit could be a SoC FPGA with separated hardware FPGA circuit (configured with predefined operations) and a hardware processor such as an ARIV! based HPS, executing software algorithms such as image blob analysis. The FPGA unit will trigger a signal as soon as that partial data is ready to be process and pushed in memory. The hardware/software processor could then start its software computation before waiting other sets of data including other blob positions. The overall process can also be parallelized.

L. Connections of Main Elements and Sub Elements of Invention

In a typical optical tracking setup, each camera (11) of the optical tracking system (10) is sensing fiducials that are m the field of view. Camera sensors—typically CMOS—are connected to a low-level tracking engine (101) that both detects the location of new fiducials in the images as well as tracks the previously detected fiducials. This action is realized by estimating the position of several windows in the image where the fiducials are expected to be located. The chapter "Example of heuristic for marker tracking in the camera sensor images" detailed hereunder in the description presents a possible implementation of such an algorithm. Partial images are readout from the sensors (I 06) and further transferred to an image compression module (107) that will reduce the memory footprint (size) of the image. This compression will also enable to later process the image without requiring a partial/full decompression (140). The chapter: "Example of algorithm to retrieve fiducials centroid in compressed partial images" hereunder presents a possible implementation of such an algorithm. Compressed partial images are further transferred to the main memory (110). The processing module is informed that new data are available either by an internal signaling system in case of an embedded processing (13) or by transmission means (USB, Ethernet, Wi-Fi, etc.) in case the processing is realized on an external PC (30). The compressed data processing unit (140) first segments the image depending on the intensity of the pixels (141) directly using the compressed images as input—without decompressing the data-, detects blobs (142) out of segmented image, defines their centroids, finds the right and left correspondence (143), and determines their 3D position by mean of triangulation (144). The correspondence between the cloud of 3D points and the geometry of the markers is further performed if the fiducials are affixed to markers (20, 21). This step is called geometry matching (145). Pose data are computed (146) and are further transferred (127) to the end-user application (130). The end-user application will format the measurements according to the interface. For example, it will inform the surgeon on the trajectory of a biopsy needle, on the position of a digitizer (20) with respect to the patient (40), etc.

M. Alternative Embodiments of Invention

If the invention comprises only the windowing mechanism, it enables the readout time to be reduced. It has the consequences to diminish the overall latency and/or to increase the update rate. As presented later, a typical configuration without windowing will run at 32 Hz due to the communication time to transfer the images. From several experimental setups, adding the windowing mechanism will increase the frame rate by a factor comprises between 30% to 100% (41.6 Hz to 64 Hz) depending on the fiducials configuration.

If the invention comprises only the compression mechanism, it enables to transfer the images at a higher frame rate (typically 335 Hz with 4-ms latency with an Atracsys fusionTrack™ system) compared to the 32 Hz without compression. High frame rate enables new types of application like integrating the optical tracking in the control loop of a robotic system.

Combining the windowing and compression mechanism (also called the overdrive mode) enables to get the performances of a high-end system (typically 1000 Hz with 3 ms latency for an Atracsys fusionTrack™) with mid-range components and with only few hardware modifications of a conventional tracking system. This allow an overall cost reduction of the hardware.

In an embodiment of the invention, the overdrive mode could be used to add tracking features on conventional monocular or stereo video camera. By conventional, one mean grayscale or color cameras acquiring full images and working in the visible and/or near IR spectrum. These cameras could have illumination rings around their lenses or not. In this embodiment, tracking images are interleaved between standard camera images In a single camera configuration, an algorithm like "Model-based object pose in 25 lines of code», Dementhon, 1995 could be used to estimate the pose of an object based on 4 or more fiducials which are located on the object/subject to track. By using the overdrive mode tracking will require fewer processing in the camera electronics and a low transmission bandwidth. As such, the overall frame rate of this hybrid tracking/conventional camera will be almost the frame rate of a conventional one. In the other hand, if the dual tracking and normal acquisition are integrated in a conventional camera, the global update rate would be two times less (as the entire tracking image needs to be transferred without compression).

An example of application of the previous embodiment is head tracking with a single (or alternatively a stereo) camera. The user wears glasses that have multiple fiducials attached. A camera with the overdrive mode enables to track head movements (respectively eyes positions) at fast update rate/low latency. A hybrid camera could be used to track and acquire images simultaneously. Hybrid acquisition could be used to operate simultaneously tracking of the glasses and a video acquisition (e.g. video conference). Estimation of eyes position could be used to drive an autostereoscopic 3D screen.

A similar hybrid approach could be used to track the head of a user with one or more fiducials located on the head (e.g. on glasses, hat, etc.) and simultaneously use image processing on conventional images to detect other features like eye, nose, mouth. These new detected features enable to refine the initial pose estimation of the tracking. Alternatively tracking of fiducials enable to bootstrap the feature detection in the images and/or make it faster.

In an embodiment of the invention, instead of having rings to illuminate reflective fiducials, active LEDs could be wirelessly synchronized (optical synchronization, Bluetooth, Li-Fi, etc.) to the camera(s) acquisition so that LEDs are active only when the camera is sensing photons. This mechanism enables to have a hybrid camera (tracking/image acquisition) as previously described by just using an existing camera hardware. Such cameras could be webcams, industrial cameras, security cameras, etc.

In an embodiment of the invention, the hybrid camera is used for security applications. Tracking is performed to check if objects (equipped with one or more fiducials) have moved or to estimate specific parameters within the field of view (e.g. the position of the floor, door, restricted area, etc.).

In an embodiment of the invention, instead of tracking the active/passive fiducials previously described, the system is extracting and tracking SIFT (Scale-Invariant Feature Transform) features at high frame rate on partial image using the windowing mechanism. The hybrid mode would enable to acquire complete images interleaved with partial images. Both rates could be independently configured (synchronously or asynchronously). Any other image feature could alternatively be used (e.g. contour/edge descriptor, color/texture descriptor, etc.).

In an embodiment of the invention, instead of tracking fiducials, the system may be capturing high-speed general purpose ID signals (e.g. spectroscopy). Using a 2D sensor (as presented in this invention) instead of ID one may be interesting either to be able to parallelize the processing (e.g. having multiple 1D signals on the 2D sensor) and/or to be able to correct the perfect alignment of the signal on the image sensor which is not possible with a 1D sensor. The overdrive mechanism enables to increase the overall update rate (data rate) and to reduce the latency.

In an embodiment of the invention, the windowing heuristic could input information provided by external sensors like Internal Measurement Units (IMUs). IMUs have the ability to work at higher frame rate or with an interleaved data acquisition. As such, it is possible to extrapolate the position of a fiducial in the camera reference frame in order to narrow the windowing search. Such an approach will reduce the search zones (windows), make the detection heuristic more robust and enable a higher frame rate/reduced latency In an embodiment of the invention, the described optical tracking system can be used m a medical robotic application. Fiducials (respectively markers) would be placed on the robot (e.g. on its end-effector) and on the patient. Robot control would include the data from the high-speed, low latency optical tracking system, for example, to compensate in real-time for the movements of the patient during the procedure.

In an embodiment of the invention, the described optical tracking system can be used m an intelligent tool robotic application. This configuration is very similar to the previous one except that the surgeon will hold the robot. In addition to the previous benefits, this setup enables to have the surgeon move faster (and more naturally) as the latency is reduced and update speed increased.

What has been described and illustrated herein is a preferred embodiment of the invention along with some of its variations. The terms, descriptions and figures used herein are set forth by way of illustration only and are not meant as limitations. Those skilled in the art will recognize that many variations are possible within the spirit and scope of the invention in which all terms are meant in their broadest, reasonable sense unless otherwise indicated. Any headings utilized within the description are for convenience only and have no legal or limiting effect.

Exemplary embodiments have been described to provide an overall understanding of the principles of the structure, function, manufacture, and use of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments and that the scope of the present invention is defined not solely by the claims. The features illustrated or described in connection with one exemplary embodiment may be combined with the features of other embodiments. Such modifications and variations are intended to be included within the scope of the present invention. A number of problems with conventional methods and systems are noted herein and the methods and systems disclosed herein may address one or more of these problems. By describing these problems, no admission as to their knowledge in the art is intended. A person having ordinary skill in the art will appreciate that, the scope of the present invention is not so limited. Moreover, while this invention has been described in conjunction with a number of embodiments, it is evident that many alternatives, modifications and variations would be or are apparent to those of ordinary skill in the applicable arts. Accordingly, it is intended to embrace all such alternatives, modifications, equivalents and variations that are within the scope of this invention.

INDEX OF ELEMENTS

10: Optical Tracking System
11: Camera
12: Ring of Ir Leds
13: Internal Cpu Ressources
20: Tracked Tools
21: Marker
22. Fiducials
30: Pc System
31: (touch-)screen
32: Wired Connection To Pc
33: Connection Between Screen And Pc
34: Internal Connection To Embedded Cpu
40: Tracked Subject
50: Operator
51: Robot
52: End Effector of the Robot
53: Surgical Tool
54: Intelligent (Robotic) Tool
60: Tablet
61: wireless Connection To Optical Tracking System
70: N/A
80: N/A
90: N/A
100: Camera Sensor
105. Pixel Readout To Memory
106: Partial Images Readout To Image Compressor
107: Image Compressor
108: Transfer of Compressed Images To Memory
110: Memory
120: Data Processing
121. Image Segmentation Module
122: Blob Detection Module 123. Blob Identification Module
124: Triangulation Module
125. Geometry Matching Module
126: Pose Computation Module
127: Transfer of Pose Data To Application
130: End-user Application
140: Compressed Partial Images Processing
141. Image Segmentation Module With Partial Compressed Images
142 Blob Detection Module
143. Blob Identification Module
144. Triangulation Module
145. Geometry Matching Module
146. Pose Computation Module
147. Transfer of Pose Data To Application Annex 1: Example of Heuristic for Marker Tracking in the Camera Sensor Images.

The use of robotics in surgical application is on the rise. These new applications are by design more latency-constrained than traditional applications of computer assisted surgery systems. Indeed, smaller latencies are necessary for robots to react to external events on time. This is especially critical in surgical applications where human life is at stake. The high-end tracking solution of the company Atracsys is called the fusionTrack™. It is able to stream and process stereoscopic images at more than 330 Hz. While its frame rate is fairly high, customers pointed out that its average latency of 4 milliseconds doesn't meet their real-time requirements. To reduce it to 3 milliseconds, we are going to:

1. roughly break down the contributions to the latency of the fusionTrack™ to show that the bottleneck is the readout of the CMOS sensor (section 1),
2. devise a heuristical windowing predictor to track blobs at a higher frame rate (section 2).

A1. Latency Break Down of the fusionTrack™

We define the latency of a stereoscopic tracking system as the time elapsed between the images exposure and their delivery, after processing, to the user application. On the fusionTrack™, this time can roughly be divided in the exposure time, the readout time, the compression time, the memory access time, the transmission time and the processing time. Some of these contributors are pipelined: for instance, images are compressed and stored in memory by the hardware as they are read out from the sensor. However, we have to pay the full price of the sensor readout, transmission and processing time.

Figure 8:
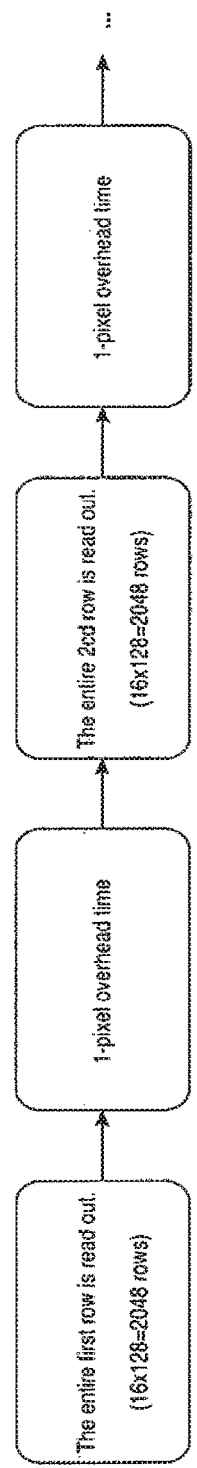
FIG. 8: illustrates the readout procedure of a CMOSIS CMV2000.

The CMOSIS CMV2000, the CMOS sensor used in the fusionTrack™, already attempts to amortize the readout cost by providing 16 readout channels to read 2048×1088×10-bit frames. More precisely, 10-bit pixels are burst out sequentially in batches of 128 adjacent columns from each channel. FIG. 8 outlines this readout process.

The readout clock being a 240-Mhz DDR clock, the time to read out a single pixel is therefore:

$$10 \text{bits/pixel} \times 2.083 ns/\text{bit} = 20.8 ns.$$

So, the time to read a full row is a full row is $$10 \text{bits/pixel} \times 128 \text{pixels/burst} \times 2.083 ns/\text{bit} = 2.7 \mu s.$$

The total time to read a full frame follows:

$$1088 \text{rows/frame} \times (20.83 + 2667) ns/\text{row} = 2.9 ms.$$

In conclusion, the readout time accounts for roughly 75% of our 4-ms latency. By Amdahl's law, breaking down the rest of the contributions is unnecessary as we would need to entirely annihilate it to reach our 3-ms latency goal.

A2. Height Rows to Rule them all

The CMOSIS CMV2000 features row-windowing capabilities. More precisely, 8 ranges of contiguous rows can be read out from the sensor instead of the full picture. Our idea is to limit the section of the frame being read out by predicting the row-windows of interests, i.e. those containing tracked blobs, of the next frame based on the current frame. This work is based on the following assumptions:

1. reading one nth of the frame will roughly divide the readout time by n, meaning that
   a. the time to write and for the sensor to adopt the new row-windowing configuration is negligible, and
   b. the next frame row-windowing can be computed during the readout of the current frame.

Each of these assumptions are to be discussed in the following sections.

A2.1. Configuration Overhead

The row-windowing configuration is stored in the sensor's registers programmed over SPI. The SPI clock has 48-MHz frequency and up to 34 8-bit registers need to be programmed (2 specifying the overall 16-bit number of lines being read out and 4 per windows). Writing an 8-bit register takes requires 16 bits to be written (1 R/\V bit, 7 address bits and 8 data bits). As multiple SPI writes can be burst, the time to update the row-windowing configuration can be estimated as $$34 \text{ registers} \times 16 \text{bits/register} \times 20.833 ns/\text{bit} = 11.3 \mu s.$$

Being more than 270 times smaller than the current readout time, this appears to validate assumption 1a.

A2.2. A Row-Windowing Heuristic for Optical Tracking

In this section, we devise a heuristic for row-windowed optical tracking. As it is to be implemented in programmable hardware, the heuristic must be simple enough to limit implementation cost.

As a starting point, simplistic approach would be to evenly divide the frame into 8 row-windows and activate them on frame i+1 based on the content of frame i. In other words, for each of the 8 evenly-divided row-windows, we activate it on frame i+1 if the one on frame i contains a tracked blob. While this approach works, it has numerous downsides, the first of which being its lack of effectiveness if tracked blobs are smalls compared the height of a uniform row-windows. To solve this problem, we might look at the content of a given row-window on frame i and update its boundaries so that it is clamped to its content on frame i+1. While this will improve the heuristic's performance, it greatly diminishes its reliability as moving blobs will quickly be lost. Therefore, the boundary clamping must be performed so as to allocate a safety zone on top and bottom of the content of a given row-window. Determining the height of this safety zone is dependent on the user application. More precisely, it will depend on the speed of the blobs and the optical jitter of the sensor.

Finally, another issue is that untracked blobs might show up in invisible area of the frame as the predictor doesn't have access to the whole frame. A first solution might be to ignore this problem and make sure that new blobs are never introduced for the duration of the experiment. This scenario results in an overhead latency only in the initialization phase until all the blobs are tracked. However, m the undesirable event of the loss of a blob whether it is because of its speed or because it has gone out of the working volume, this would force the user to go back to the initialization phase. In conclusion, choosing whether to solve the problem of invisible blobs should be left to the user. Therefore, we considered two approaches:

1. at given intervals, a full frame can be captured, or
2. a sliding row-window can scan the frame continuously.

The first approach generates spikes in the readout period. It means that, for the duration of a frame, the system might rollback to its original 4-ms latency. This is unacceptable as, if it coincides with an event of interest for the robot controller, this would result in non-conforming feedback latency. We therefore restricted our research to the second approach.

Finally, note that while this potentially validates assumption 1 b, we still need to show that this approach works in practice and come up with a design that parallelize the frame readout and the prediction detailed above.

A.23. Results

Figure 9:
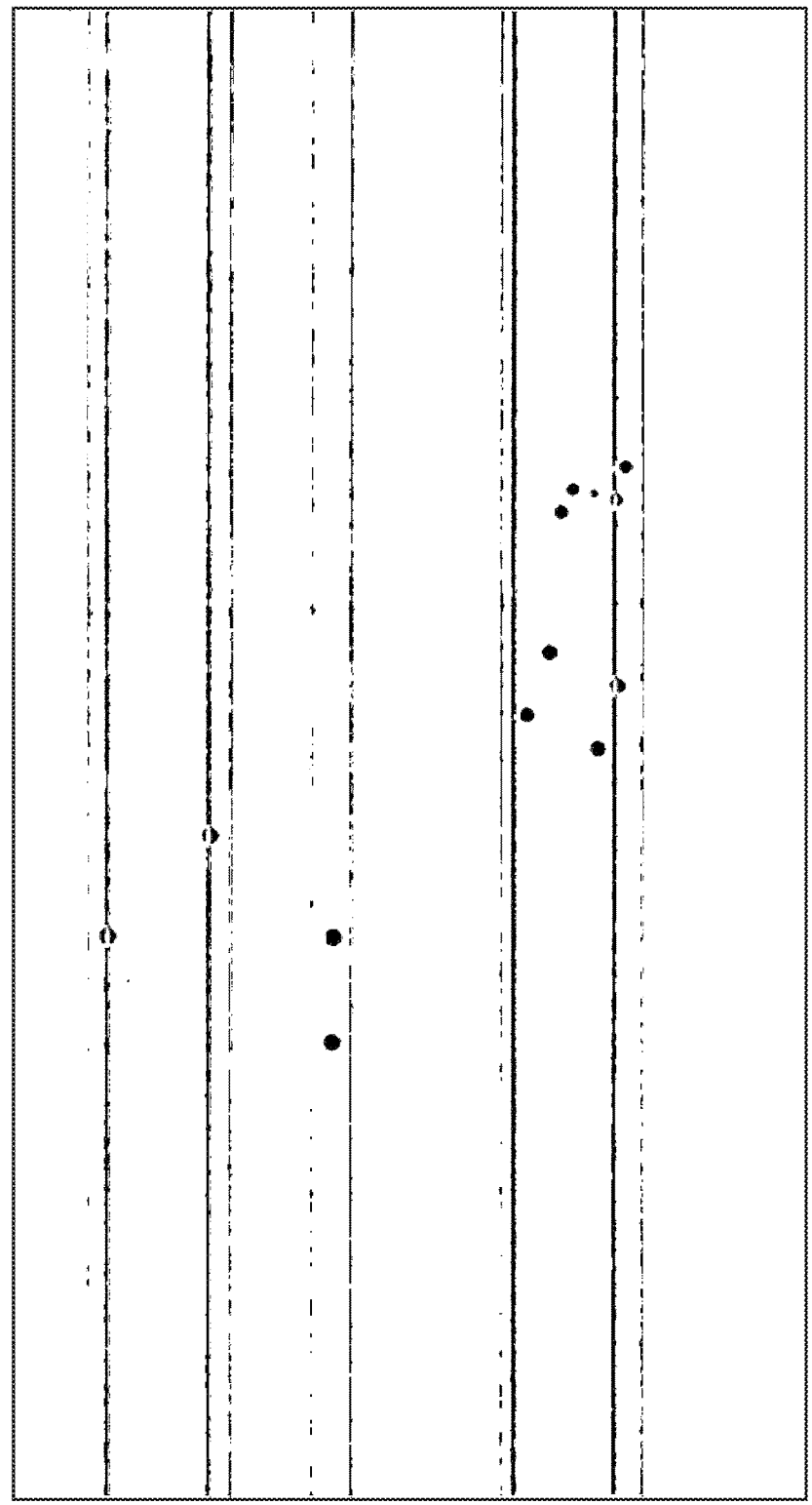
FIG. 9: illustrates a simulator in action. The white disks are the tracked blobs, the red areas (or clear lines) are the row-windows and the black (or dark) area is the invisible portion of the frame.
Figure 10:
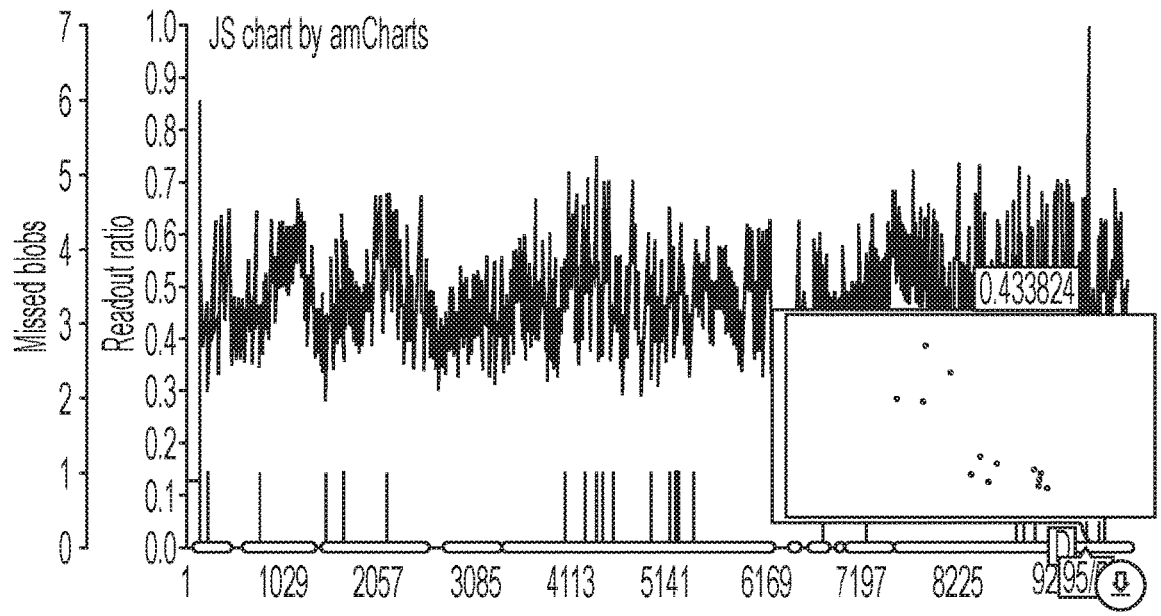
FIG. 10: illustrates the HTML output of a simulator. The top graph shows the curve of the readout ratio during the capture. The user can query events to see screenshots using his mouse. The bottom graph is a histogram to assess the distribution of the readout ratio.
Figure 10:
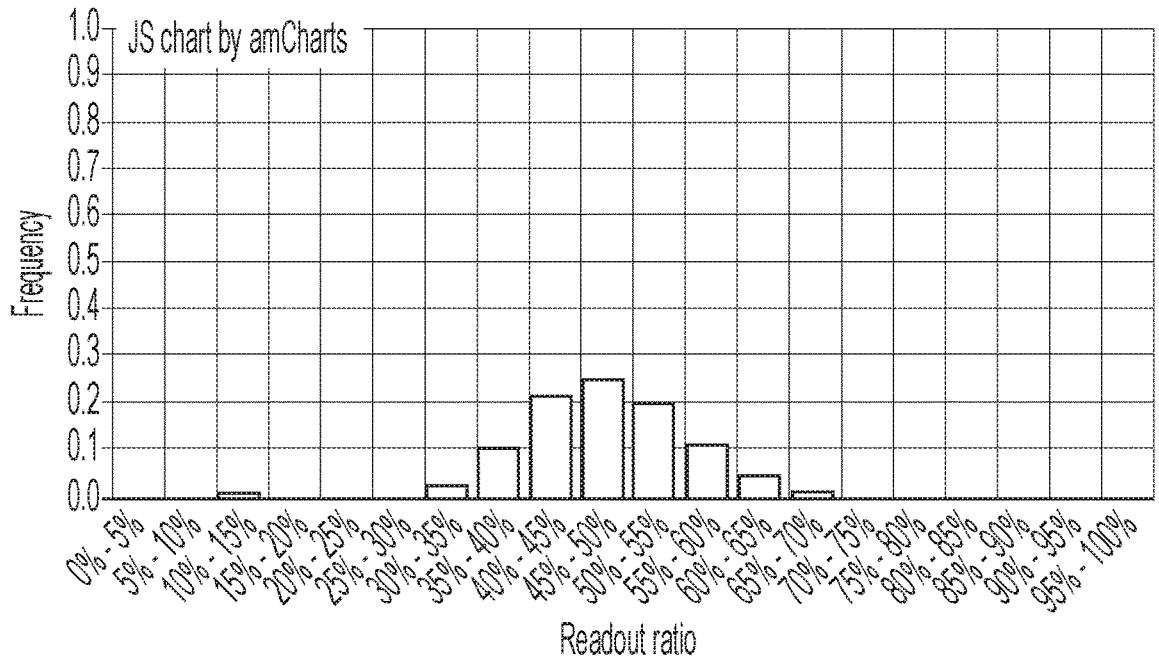

To assess the impact of the row-windowing heuristic described in section A2.2, we have implemented a simulator. It tries to predict the row-windowing configuration of frame i+1 based on the content of frame i. For a qualitative assessment, it graphically displays the row-windows and the tracked blobs in real time, and saves screenshots of events that needs further attention (change in the readout ratio, i.e. the portion of the frame being read out, or invisible blobs). Finally, it outputs an automated HTML report that shows the readout ratio curve, histogram and the blobs that are lost. FIG. 9 shows a screenshot of the simulator, namely the simulator in action, where the white disks are the tracked blobs, the red/clear areas or lines are the row-windows and the black/dark areas are the invisible portion of the frame. FIG. 10 shows an example of a generated report.

In conclusion, we showed that our heuristic for row-windowed optical tracking is valuable provided the environment is controlled. To overcome the environmental risk, a readout time monitoring mechanism must be added to the acquisition pipeline in addition of the row-windowing predictor. This would allow the end-user to detect if it is basing a decision on outdated data depending on the application-specific time constraints.

FIG. 10 illustrates an HTML output of the simulator. The top graph shows the curve of the readout ratio during the capture. The user can query events to see screenshots using his mouse. The bottom graph is a histogram to assess the distribution of the readout ratio.

Annex 2: Example of Algorithm to Retrieve Fiducials Centroid in Compressed Partial Images In delegated processing (as presented in FIG. 1), image data are entirely processed on the computer. This is not a limitation with modern processor as the still following the Moor's law. The only drawback is the transmission of the data from the tracking system to the computer. If we consider a Gigabit Ethernet connection—which is now available on any PC—and a system composed of two Full-HD grayscale cameras with a pixel depth of 8 bits, we get a maximum theoretical update rate of:

$$1024\textasciicircum 3/(8*2*1920*1080)=32 Hz$$

A good way to improve the update rate would be to compress the images in the tracking systems and decompress them in the computer. This approach would unfortunately require much more data processing means on the computer as images must be first decompressed before being further processed.

Modern optical tracking requires precision and speed. Precision is achieved by using cameras with high resolution and fast update rate is necessary to reduce the latency between a real movement and its corresponding measurement in the application.

As an example, the speed of a robotic system driven by optical tracking is directly linked to the update rate and latency of the tracking system.

We propose to solve the drawback of the decompression overhead on the computer by providing a compression representation that can directly be used by the processing unit (e.g. PC) without requiring any decompression.

A first advantage of this approach is that the update rate is limited by the compression efficiency (as the transmission is the weakest link in the processing chain).

Another advantage of our invention is as the compressed image can be more efficiently stored m the cache of the processor, it will be process faster.

Practically, with our compression we have developed, we get a maximum update rate improved by a factor 10 in a typical configuration (see Figure A1.2). This compression algorithm is only able to compress full 8 bits images. It is presented below:

The compression algorithm produces the following output:
the output data consists of 8 bits, the MSB discriminates between white and black pixels:
1 means the 7 LSBs are the original pixel intensity divided by 2;
means the 7 LSBs are the number of consecutive black pixels. The following exceptions exist:
0x80 means 128 consecutive black values;
0x00 followed by a value encoded on 2 bytes (little endian, i.e. LSBs first) indicates a number of completely black lines. The address of this 0x00 byte must be a multiple of 16;
any other 0x00 are ignored (this is a no-op character, used by the FPGA which must write multiples of 16 bytes).

The advantage of such a compression is that it is easy to get the (x,y) position of a blob directly in the compressed image (without need for decompression).

This representation enables to efficiently extract blobs from compressed images by using an adapted version of a line-scan fill algorithm. The scanline fill algorithm (https://en.wikipedia.org/wiki/Flood_fill#Scanline_fill) is an optimization of the flood fill algorithm. Instead of pushing each potential future pixel coordinate on the stack, it inspects the neighbor lines (previous and next) to find adjacent segments that may be filled in a future pass; the coordinates (either the start or the end) of the line segment are pushed on the stack. In most cases this scanline algorithm is at least an order of magnitude faster than the per-pixel one.

We are able to run the described configuration at a speed of 335 Hz which is more than 10 times higher than the non-compressed version.

The invention claimed is:

1. A method for improved optical tracking, the method comprising:
    identifying one or more of a plurality of windows based on a detection heuristic, wherein the identified one or more of the plurality of windows correspond to an estimated signal position within at least one optical sensor;
    generating, by the at least one optical sensor, sensor data in response to detection of at least one signal, wherein the at least one signal comprises at least one fiducial attached to a marker;
    extracting a portion of the sensor data based on the identified one or more of the plurality of windows, wherein the extracted portion of the sensor data corresponds to a partial image;
    determining at least one characteristic of the at least one signal from the partial image;

compressing at least the extracted portion of the sensor data to generate a compressed image;
determining at least one of a position or an orientation of the marker from the compressed image; and
transmitting the determined at least one characteristic of the at least one signal and the determined at least one of the position or the orientation of the marker through a communication channel to an application.

2. The method as defined in claim 1, wherein the at least one signal comprises two or more one dimensional (1D) signals, the at least one optical sensor comprises a two dimensional (2D) complementary metal oxide semiconductor (CMOS) image sensor, and the method further comprises processing at least the extracted portion of the sensor data in parallel for the two or more 1D signals.

3. The method as defined in claim 1, further comprising:
tracking a plurality of signal positions of a plurality of signals over a historical time period prior to identifying the one or more of the plurality of windows; and
generating the detection heuristic based on the tracking.

4. The method as defined in claim 1, wherein the partial image comprises partial sensor data sufficient for determining the at least one of the position or the orientation of the marker.

5. The method as defined in claim 1, further comprising segmenting the compressed image depending on an intensity of a plurality of pixels to form a segmented image.

6. The method as defined in claim 5, further comprising:
detecting one or more blobs in the segmented image; and
determining the position of the one or more blobs.

7. The method as defined in claim 1, wherein the application comprises a navigation application configured to track the marker.

8. The method as defined in claim 1, wherein at least one of the extracted portion of the sensor data or the determined at least one of the position or the orientation of the marker is used to control a robotic structure configured for use in a surgical application.

9. The method as defined in claim 1, wherein the at least one optical sensor is a plenoptic camera comprising an array of micro-lenses placed in front of an array of sensors, each micro-lens and one or more corresponding pixels of the array of sensors form a micro-camera, and information from the micro-camera is used to determine the at least one of the position or the orientation of the marker in the compressed image.

10. A device for improved optical tracking, comprising:
at least one optical sensor configured to generate sensor data in response to detection of at least one signal, wherein the at least one signal comprises at least one fiducial attached to a marker; and
at least one processing unit configured to:
identify one or more of a plurality of windows based on a detection heuristic, wherein the identified one or more of the plurality of windows correspond to an estimated signal position within at least one optical sensor;
extract a portion of the sensor data based on the identified one or more of the plurality of windows, wherein the extracted portion of the sensor data corresponds to a partial image;
determine at least one characteristic of the at least one signal from the partial image;
compress at least the extracted portion of the sensor data to generate a compressed image;
determine at least one of a position or an orientation of the marker from the compressed image; and
transmit the determined at least one characteristic of the at least one signal and the determined at least one of the position or the orientation of the marker through a communication channel to an application.

11. The device as defined in claim 10, wherein the at least one signal comprises two or more one dimensional (1D) signals, the at least one optical sensor comprises a two dimensional (2D) complementary metal oxide semiconductor (CMOS) image sensor, and the processing unit is further configured to process at least the extracted portion of the sensor data in parallel for the two or more 1D signals.

12. The device as defined in claim 10, wherein the processing unit is further configured to:
track a plurality of signal positions of a plurality of signals over a historical time period prior to identifying the one or more of the plurality of windows; and
generate the detection heuristic based on the tracking.

13. The device as defined in claim 10, wherein the partial image comprises partial sensor data sufficient for determining the at least one of the position or the orientation of the marker.

14. The device as defined in claim 10, wherein the processing unit is further configured to segment the compressed image depending on an intensity of a plurality of pixels to form a segmented image.

15. The device as defined in claim 14, wherein the processing unit is further configured to:
detect one or more blobs in the segmented image; and
determine the position of the one or more blobs.

16. The device as defined in claim 10, wherein the application comprises a navigation application configured to track the marker.

17. The device as defined in claim 10, wherein at least one of the extracted portion of the sensor data or the determined at least one of the position or the orientation of the marker is used to control a robotic structure configured for use in a surgical application.

18. The device as defined in claim 10, wherein the at least one optical sensor is a plenoptic camera comprising an array of micro-lenses placed in front of an array of sensors, each micro-lens and one or more corresponding pixels of the array of sensors form a micro-camera, and information from the micro-camera is used to determine the at least one of the position or the orientation of the marker in the compressed image.

19. A method, comprising:
identifying one or more of a plurality of windows based on a detection heuristic, wherein the identified one or more of the plurality of windows correspond to an estimated signal position within at least one optical sensor;
generating, by the at least one optical sensor, sensor data in response to detection of at least one signal, wherein the at least one signal comprises at least one fiducial attached to a marker;
extracting a portion of the sensor data based on the identified one or more of the plurality of windows, wherein the extracted portion of the sensor data corresponds to a partial image;
compressing at least the extracted portion of the sensor data to generate a compressed image;
determining a position or an orientation of the marker from the compressed image; and
transmitting the position or the orientation of the marker through a communication channel to an application.

20. The method as defined in claim 19, wherein the at least one signal comprises two or more one dimensional (1D) signals, the at least one optical sensor comprises a two dimensional (2D) complementary metal oxide semiconductor (CMOS) image sensor, and the method further comprises processing at least the extracted portion of the sensor data in parallel for the two or more 1D signals.

21. The method as defined in claim 19, further comprising:
tracking a plurality of signal positions of a plurality of signals over a historical time period prior to identifying the one or more of the plurality of windows; and
generating the detection heuristic based on the tracking.

22. The method as defined in claim 19, wherein the partial image comprises partial sensor data sufficient for determining the position or the orientation of the marker.

23. The method as defined in claim 19, further comprising segmenting the compressed image depending on an intensity of a plurality of pixels to form a segmented image.

24. The method as defined in claim 23, further comprising:
detecting one or more blobs in the segmented image; and
determining the position of the one or more blobs.

25. The method as defined in claim 19, wherein the application comprises a navigation application configured to track the marker.

26. The method as defined in claim 19, wherein at least one of the extracted portion of the sensor data or the position or the orientation of the marker is used to control a robotic structure configured for use in a surgical application.

27. The method as defined in claim 19, wherein the at least one optical sensor is a plenoptic camera comprising an array of micro-lenses placed in front of an array of sensors, each micro-lens and one or more corresponding pixels of the array of sensors form a micro-camera, and information from the micro-camera is used to determine the position or the orientation of the marker in the compressed image.

28. A device, comprising:
at least one optical sensor configured to generate sensor data in response to detection of at least one signal, wherein the at least one signal comprises at least one fiducial attached to a marker; and
at least one processing unit configured to:
identify one or more of a plurality of windows based on a detection heuristic, wherein the identified one or more of the plurality of windows correspond to an estimated signal position within at least one optical sensor;
extract a portion of the sensor data based on the identified one or more of the plurality of windows, wherein the extracted portion of the sensor data corresponds to a partial image;
compress at least the extracted portion of the sensor data to generate a compressed image;
determine a position or an orientation of the marker from the compressed image; and
transmit the position or the orientation of the marker through a communication channel to an application.

29. The device as defined in claim 28, wherein the at least one signal comprises two or more one dimensional (1D) signals, the at least one optical sensor comprises a two dimensional (2D) complementary metal oxide semiconductor (CMOS) image sensor, and the processing unit is further configured to process at least the extracted portion of the sensor data in parallel for the two or more 1D signals.

30. The device as defined in claim 28, wherein the processing unit is further configured to:
track a plurality of signal positions of a plurality of signals over a historical time period prior to identifying the one or more of the plurality of windows; and
generate the detection heuristic based on the tracking.

31. The device as defined in claim 28, wherein the partial image comprises partial sensor data sufficient for determining the position or the orientation of the marker.

32. The device as defined in claim 28, wherein the processing unit is further configured to segment the compressed image depending on an intensity of a plurality of pixels to form a segmented image.

33. The device as defined in claim 32, wherein the processing unit is further configured to:
detect one or more blobs in the segmented image; and
determine the position of the one or more blobs.

34. The device as defined in claim 28, wherein the application comprises a navigation application configured to track the marker.

35. The device as defined in claim 28, wherein at least one of the extracted portion of the sensor data or the position or the orientation of the marker is used to control a robotic structure configured for use in a surgical application.

36. The device as defined in claim 28, wherein the at least one optical sensor is a plenoptic camera comprising an array of micro-lenses placed in front of an array of sensors, each micro-lens and one or more corresponding pixels of the array of sensors form a micro-camera, and information from the micro-camera is used to determine the position or the orientation of the marker in the compressed image.

* * * * *